United States Patent [19]

Evans et al.

[11] Patent Number: 5,185,462
[45] Date of Patent: Feb. 9, 1993

[54] PRODUCTION OF CARBOXYLIC ACIDS AND ESTERS THEREOF

[75] Inventors: John Evans, Romsey; Steven L. Scruton, Boreham Wood, both of England

[73] Assignees: BP Chemicals Limited; The University of Southampton, both of London, England

[21] Appl. No.: 771,789

[22] Filed: Oct. 4, 1991

Related U.S. Application Data

[63] Continuation of Ser. No. 639,323, Jan. 9, 1991, abandoned, which is a continuation of Ser. No. 517,481, Apr. 30, 1990, abandoned, which is a continuation of Ser. No. 141,056, Jan. 5, 1988, abandoned.

[30] Foreign Application Priority Data

Jan. 8, 1987 [GB] United Kingdom ............... 8700402

[51] Int. Cl.$^5$ ............................................. C07C 51/10
[52] U.S. Cl. .................................. 560/232; 562/519; 554/128
[58] Field of Search ................ 562/519; 560/232; 260/413, 410.9 R; 554/128

[56] References Cited

U.S. PATENT DOCUMENTS

| | | | |
|---|---|---|---|
| 1,946,258 | 2/1934 | Carothers et al. | 562/519 |
| 3,769,329 | 10/1973 | Paulik et al. | 562/519 |
| 3,907,852 | 9/1975 | Oswald | 260/429 R X |

FOREIGN PATENT DOCUMENTS 1233121 5/1971 United Kingdom.
1342877 1/1974 United Kingdom.

*Primary Examiner*—Arthur C. Prescott
*Attorney, Agent, or Firm*—Brooks Haidt Haffner & Delahunty

[57] ABSTRACT

A process for the production from an alcohol having n carbon atoms, wherein n is a number from 1 to 20, of a carboxylic acid having n+1 carbon atoms and/or an ester of the alcohol having n carbon atoms with the carboxylic acid by reacting the alcohol at a temperature of at least 50° C. with carbon monoxide in the presence of a noble metal-containing heterogeneous catalyst and a halogen or halogen compound promoter characterized in that the catalyst comprises a noble metal component bonded to an inorganic oxide having surface hydroxyl groups through the intermediacy of a silicon compound which is condensible with the hydroxyl groups of the inorganic oxide and has either (i) at least one nitrogen or phosphorus-containing functional group capable of coordinating with the noble metal component or (ii) a functional group capable of reacting further with a nitrogen- or phosphorus-containing functional group capable of coordinating with the noble metal component thereby to bond the nitrogen- or phosphorus-containing functional group to the silicon compound.

10 Claims, No Drawings

PRODUCTION OF CARBOXYLIC ACIDS AND ESTERS THEREOF

This application is a continuation of application Ser. No. 07/639,323, filed Jan. 9, 1991, now abandoned, which is continuation of Ser. No. 07/517,481, filed Apr. 30, 1990, now abandoned, which is continuation of Ser. No. 07/141,056, filed Dec. 5, 1988, now abandoned.

The present invention relates in general to the production of carboxylic acids and/or esters thereof and in particular to a process for the production from an alcohol having n carbon atoms of a carboxylic acid having n+1 carbon atoms or an ester of the alcohol having n carbon atoms with the acid by reacting the alcohol at elevated temperature with carbon monoxide in the presence as catalyst of a noble metal component and a promoter substance which is halogen or a halogen compound.

The carboxylation of alcohols to carboxylic acids and/or esters thereof in the presence of a noble metal component as catalyst and a halide promoter has been known for some considerable time, see for example GB-A-1185453, GB-A-1233121, GB-A-1233122, GB-A-1234641 and GB-A-1234642. Although operation of the process in homogeneous media is favoured in the aforesaid patent disclosures, there is also provision for heterogeneous catalysis either in the liquid phase or the vapour phase. For heterogeneous operation the catalysts are dispersed either on an inert support material such as alundum, activated carbon, clays, alumina, silica-alumina and ceramics, or a porous solid carrier, such as a zeolite, a solid foam, a ceramic honeycomb or a porous organic polymer. It is apparent from the prior art that metal oxides are not the preferred support materials. No attempt is made to immobilise the active catalytic component(s) on the support materials, thereby minimising leaching of the catalyst component(s).

Since the early disclosures, attempts to immobilise the catalytic component(s) on polymer substrates by reaction of appropriate functional groups attached to the polymer backbone chain with the noble metal component have been disclosed. Although such catalysts may be effective for liquid phase operation and enjoy the advantage of relatively easy separation and recovery from the liquid reaction medium, they suffer from the disadvantage that they generally undergo thermal degradation at elevated temperatures, thereby rendering them unsuitable for vapour phase operation.

A need therefore arises for a heterogeneous catalyst wherein the catalyst component(s) is (are) immobilised on an inert support, useful for both liquid phase and vapour phase operation of the process.

We have now found that catalysts comprising a noble metal component bonded to an inorganic oxide having surface hydroxyl groups through the intermediacy of a silicon compound which is condensible with the hydroxyl groups of the inorganic oxide and has either (i) nitrogen or phosphorus-containing functional groups capable of coordinating with the noble metal component or (ii) a functional group capable of reacting further with a nitrogen- or phosphorus-containing functional group capable of coordinating with the noble metal component thereby to bond the nitrogen- or phosphorus-containing functional group to the silicon compound satisfy the aforesaid criteria. Although the same or similar compounds have been disclosed for use as catalysts in, for example, hydrogenation, hydroformylation, oxidation and dimerisation processes, their use as alcohols carbonylation catalysts is in our experience novel.

Accordingly, the present invention provides a process for the production from an alcohol having n carbon atoms, wherein n is a number from 1 to 20, of a carboxylic acid having n+1 carbon atoms and/or an ester of the alcohol having n carbon atoms with the carboxylic acid by reacting the alcohol at a temperature of at least 50° C. with carbon monoxide in the presence of a noble metal-containing heterogeneous catalyst and a halogen or halogen compound promoter characterised in that the catalyst comprises a noble metal component bonded to an inorganic oxide having surface hydroxyl groups through the intermediacy of a silicon compound which is condensible with the hydroxyl groups of the inorganic oxide and has either (i) at least one nitrogen or phosphorus-containing functional group capable of coordinating with the noble metal component or (ii) a functional group capable of reacting further with a nitrogen- or phosphorus-containing functional group capable of coordinating with the noble metal component thereby to bond the nitrogen- or phosphorus-containing functional group to the silicon compound.

The term "noble metal" throughout this specification is used to mean rhodium, iridium, platinum, palladium, osmium and ruthenium. Of the noble metals, rhodium and iridium are preferred and rhodium is more preferred.

As regards the catalyst, the inorganic oxide may be any inorganic oxide having surface hydroxyl groups. Examples of suitable inorganic oxides include silica, alumina and the rare earth metal oxides, such as ceria. Preferred inorganic oxides include silica and alumina.

The silicon compound must contain a moiety condensible with the hydroxyl groups of the inorganic oxide. Suitably this moiety may be a —Y group wherein Y is an —OR group in which R is an alkyl group, suitably a lower alkyl group, for example a methyl or an ethyl group or Y is an ester group or a halide group. The silicon compound may in alternative (i) also contain a moiety having a nitrogen or phosphorus-containing functional group capable of coordinating with the noble metal component. Preferably the nitrogen or phosphorus-containing functional group is one capble of quaternisation. Suitably the silicon compound (i) may have the formula:

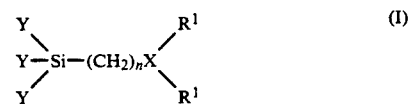

wherein the groups Y are independently —OR groups in which the groups R are alkyl groups, preferably $C_1$ to $C_4$ alkyl groups, or the groups Y are independently ester groups or halide groups, n is a number in the range from 1 to 6, X is either nitrogen or phosphorus, and the groups $R^1$ are independently either hydrogen, alkyl or together form a ring which may be either a carbocyclic or a heterocyclic nitrogen or phosphorus-containing ring. Examples of suitable silicon compounds (i) which may be used in the production of catalysts useful in the performance of the invention include

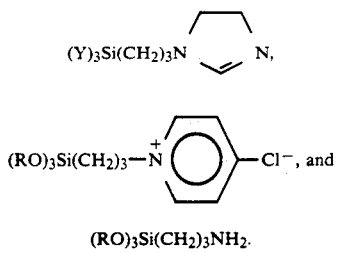

(Y)₃Si(CH₂)₃N⌒N, (A)

(RO)₃Si(CH₂)₃—N⁺⟨○⟩—Cl⁻, and (B)

(RO)₃Si(CH₂)₃NH₂. (C)

Alternatively, the silicon compound which is condensible with the hydroxyl groups of the inorganic oxide may contain a functional group capable of reacting further with a nitrogen- or phosphorus-containing functional group capable of coordinating with the noble metal component thereby to bond the nitrogen- or phosphorus-containing functional group to the silicon compound. Such a functional group may be for example a halide group, for example a chloride group, which is capable of reacting further with, for example $NR_3$ or $PR_3$, wherein R is independently hydrogen or alkyl, or together form a ring, thereby to bond the $NR_3$ or $PR_3$ to the silicon compound. An example of a suitable silicon compound is $(MeO)_3Si(CH_2)_3Cl$ which is reactable with pyridine for example after condensing with the inorganic oxide.

A preferred silicon compound is the compound (A). The noble metal component coordinated with the silicon compound may suitably take the form of an oxide, salt or coordination compound thereof.

The catalyst (i) may suitably be prepared by the steps comprising:

in a first step reacting an inorganic oxide having surface hydroxyl groups with a silicon compound having a first moiety which is condensible with hydroxyl groups and a second moiety which is a nitrogen or phosphorus-containing functional group capable of coordinating a noble metal component under conditions whereby the hydroxyl groups of the inorganic oxide react with the first moiety thereby to bond the silicon compound to the inorganic oxide, and in a second step reacting the second moiety of the product of the first step with a noble metal component, thereby to coordinate the noble metal component to the silicon compound.

In a modification of this method the noble metal component may be reacted with the second moiety of the silicon compound before this latter compound is reacted via the first moiety with the inorganic oxide.

Preferably as many of the surface hydroxyl groups of the inorganic oxide as possible are reacted with the silicon compound.

We believe, although we do not wish to be bound in any way by our belief, that under the conditions of the process, the nitrogen or phosphorus-containing functional group can be quaternised and the noble metal component is simultaneously ionised. Accordingly, the functional group may be added as such or, in a preferred embodiment of the invention it may be added in a pre-quaternised form, which may suitably be prepared by carrying out the first step of the process as hereinbefore described, in a second step reacting the product of the first step with a quaternising agent, suitably an alkyl iodide, thereby to quaternise the nitrogen or phosphorus-containing functional group and in a third step reacting the product of the second step with a noble metal halocarbonyl complex, thereby to form a noble metal halocarbonyl complex counter anion.

Alternatively, the catalyst (ii) may suitably be prepared by the steps comprising:

in a first step reacting an inorganic oxide having surface hydroxyl groups with a silicon compound having a first moiety which is condensible with hydroxyl groups and a second moiety which is a functional group capable of reacting further with a nitrogen- or phosphorus-containing compound capable of coordinating with a noble metal component under conditions whereby the hydroxyl groups of the inorganic oxide react with the first moiety thereby to bond the silicon compound to the inorganic oxide, in a second step reacting the second moiety with a nitrogen- or phosphorus-containing compound under conditions whereby the nitrogen- or phosphorus-containing compound is bonded to the silicon compound, and in a third step reacting the product of the second step with a noble metal component under conditions whereby the noble metal component is coordinatively bonded to the silicon compound.

As regards the alcohol used as feedstock, this may suitably be an aliphatic alcohol having from 1 to 20 carbon atoms including methanol, ethanol, propanol and isopropanol, the butanols, pentanols and hexanols, and also the higher alcohols such as the decanols, including isomeric forms. Preferably methanol is used as the feedstock to produce acetic acid and/or methyl acetate. The methanol may be essentially pure or may contain impurities commonly associated with commercial grades, for example water and ethanol. Polyhydric alcohols may be employed, as may also aromatic hydroxyl-containing compounds, for example phenol.

Carbon monoxide is readily available on a commercial scale and may contain impurities commonly associated therewith, for example methane, nitrogen and hydrogen, but should be substantially free of oxygen.

The promoter is a halogen or a halogen compound which may be for example a hydrogen halide, an alkyl or aryl halide, a metal halide or an ammonium, phosphonium, arsonium or stibonium halide, which may be the same or different from any halogen component already present in the catalytic component. Those containing iodine are preferred. Preferably the promoter is an alkyl iodide, for example methyl iodide.

The process may be operated in the vapour phase or the liquid phase, the liquid phase being preferred using higher alcohols as feedstock.

The process may be operated batchwise or continuously, preferably continuously employing the catalyst in the form of either a fixed or a fluidised bed.

The process is operated at elevated temperature, suitably in the range from 50 to 300, preferably from 100° to 250° C., and a pressure suitably in the range from 1 to 100, preferably from 5 to 50 barg. The Liquid Hourly Space Velocity (LHSV) for vapour or liquid, fixed or fluidised bed operation may suitably be in the range from 0.1 to 20.0, the preferred value within this range being dependent on the temperature and pressure. The molar ratio of carbon monoxide to liquid feed may suitably be in the range from 0.1:1 to 20:1, preferably from 1:1 to 10:1.

Further details regarding reactants, modes of operations and reaction conditions may be found in the aforesaid GB patent publications, the contents of which are incorporated herein by reference.

The invention will now be further illustrated by reference to the following Examples.

CATALYST PREPARATION

Catalyst A (alternative (i))

(a) Silica (FK 700; 5 g) (dried under vacuo for 48 h at 140° C. prior to use) was refluxed with $[EtO]_3Si(CH_2)_3N_2C_3H_5$ (5 g) in toluene (50 ml) and from this mixture was azeotroped toluene containing ethanol using a Dean and Stark apparatus. After 16 h the resulting yellow silica was filtered off and washed with petroleum ether (3×30 ml). The silica was transferred to a Soxhlet apparatus and extracted with diethyl ether for 16 h.

(b) Silica obtained in (a) above (5 g) was refluxed with methyl iodide (5 g) in toluene (30 ml). After 16 hours the resulting bright yellow solid was removed by filtration and washed with petroleum ether (3×30 ml). The silica was transferred to a Soxhlet apparatus and extracted with carbon tetrachloride for 16 h. The silica was dried under vacuo.

(c) Rhodium carbonyl chloride $[Rh(CO)_2Cl]_2$ (0.02 g) dissolved in methanol (10 ml) was added to silica obtained in (b) above (1.8 g). The reaction mixture was stirred for 5 minutes and the resulting brown silica removed by filtration. Its rhodium content was found by analysis to be 1.29% b.w. of dried material.

Catalyst B (alternative (i))

Rhodium carbonyl chloride, $[Rh(CO)_2Cl]_2$, (0.02 g) dissolved in methanol (10 ml) was added to silica (FK 700; 1.8 g) which had previously been dried in vacuo at 140° C. After stirring for 5 minutes the solvent was removed on a rotary evaporator.

Catalyst C (alternative (ii))

(a) Gamma-alumina (CONDEA 200 (RTM): 5 g) (dried under vacuo for 48 h at 140° C. prior to use) was refluxed with $(MeO)_3Si(CH_2)_3Cl$ (5 g) in toluene (50 ml) and from this mixture was azeotroped toluene and methanol using a Dean and Stark apparatus. After 16 h the resulting silica was filtered off and washed 3 times with petroleum ether (30 ml). The silica was then transferred to a Soxhlet apparatus and extracted with diethyl ether for 16 h.

(b) Alumina obtained from (a) above (5 g) was refluxed with pyridine (30 ml). After 16 h the resulting white solid was filtered off and washed with dichloromethane (3×30 ml) before Soxhlet extraction with diethylether for a further 16 h. The resulting alumina was dried in vacuo.

(c) $[Rh(CO)_2Cl]_2$ (0.02 g) was dissolved in methanol (10 ml) and then added to the dried alumina from (b) above (1.8 g). The mixture was stirred for 5 minutes and the resulting brown alumina removed by filtration. The catalyst was found to contain 0.37% rhodium b.w. of dried material.

Catalyst D (alternative (i))

The procedure used for the preparation of Catalyst B was followed except that the silica (FK 700) was replaced by gamma-alumina (CONDEA 200; 1.8 g).

THE CARBONYLATION OF METHANOL

Example 1

Catalyst A (2 ml) was loaded into a tubular reactor of 6-7 mm internal diameter and was tested in the carbonylation of a feedstock containing methanol and methyl iodide.

The feedstock was pumped to a preheated/vapouriser where it was evaporated and mixed with a flowing stream of carbon monoxide. The combined vapour/gas mixture was passed over the catalyst, and the outlet stream was analysed by gas chromatography at predetermined time intervals, prior to cooling and condensation of the liquid products. The reactor was heated by a tubular furnace and the temperature measured by a thermocouple inserted into the catalyst bed. Pressure in the reactor was set and maintained by means of a batch pressure regulator. Liquid and gas feed rates to the vapouriser could be readily varied from 0-10 ml/h and 0-200 ml/m respectively.

The following conditions were established:
LHSV = 1
CO:MeOH:MeI molar ratio = 60:20:1
Total Pressure = 9 barg
Temperature = 186° C.

The temperature was then held at 186° C. for about 4 h before being increased. This procedure was repeated twice more before the temperature was reduced again to 186° C. Analysis of the product stream at hourly intervals then allowed the results presented in Table 1 to be calculated. With reference to Table 1, conversion is defined as the fraction (expressed as a percentage) of methanol converted to acetic acid, methyl acetate, dimethyl ether and methane, assuming that methyl acetate contains one converted and one unconverted methanol moiety (i.e. conversion does not take into account methanol converted by esterification).

TABLE 1

| Temperature °C. | | Conversion* | Product Proportions | | |
|---|---|---|---|---|---|
| Furnace | Reactor Bed | (%) | MeOAc | AcOH | MeO |
| 180 | 186 | 16.1 | 14.4 | 0.8 | 0.1 |
| 200 | 211 | 34.4 | 31.0 | 1.6 | 0.1 |
| 220 | 231 | 48.5 | 35.0 | 10.6 | 0.1 |
| 240 | 251 | 49.8 | 32.9 | 14.3 | 0.1 |
| 180 | 186 | 38.4 | 22.6 | 13.4 | 0.1 |

*Major product was methyl acetate

COMPARISON TEST 1

Catalyst B (2 ml) was tested for the carbonylation of methanol at ca. 180° C. and 9 barg using the procedure of Example 1. The conversion to carbonylated products was less than 1%.

This test demonstrates that rhodium supported on silica is not active as a catalyst and is included only for the purpose of comparison.

EXAMPLE 2

Catalyst C (2 ml) was tested in the carbonylation of methanol at 181° C., 9 barg, LHSV = 1 and a CO:MeOH:MeI molar ratio = 60:20:1 using the experimental procedure outlined in Example 1. The duration of the experiment was 14½ h. Methanol conversions and product proportions after different times on stream are presented in Table 2.

TABLE 2

| Time on Stream (h) | Conversion (%) | Product Proportions | | |
|---|---|---|---|---|
| | | $CH_3OCOCH_3$ | $CH_3CO_2H$ | $CH_3OCH_3$ |
| 4.5 | 10.2 | 8.5 | 1.5 | 0.1 |
| 6.5 | 9.5 | 8.1 | 1.4 | 0.1 |
| 8.5 | 9.8 | 8.4 | 1.2 | 0.1 |

TABLE 2-continued

| Time on Stream (h) | Conversion (%) | Product Proportions | | |
|---|---|---|---|---|
| | | CH$_3$OCOCH$_3$ | CH$_3$CO$_2$H | CH$_3$OCH$_3$ |
| 10.5 | 9.6 | 8.6 | 0.9 | 0.1 |
| 12.5 | 9.3 | 8.2 | 1.0 | 0.1 |
| 14.5 | 9.6 | 8.6 | 0.8 | 0.1 |

COMPARISON TEST 2

Catalyst D (2 ml) was tested in the carbonylation of methanol according to the procedure of Example 1 under the following conditions: LHSV=1, CO:MeOH:MeI molar ratio=60:20:1, pressure=9 barg and temperature=ca. 180° C. Conversion to carbonylation products was less than 1%, demonstrating that the alumina supported rhodium catalyst is not active under the conditions used.

This is not an example according to the present invention and is included for comparison purposes only.

We claim:

1. A vapor phase process for preparing a carboxylic acid having n+1 carbon atoms and/or an ester of said acid and an alcohol of n carbon atoms which process comprises:
   (1) vaporising said alcohol,
   (2) contacting the vapor of said alcohol with carbon monoxide at a temperature of at least 50° C. in the presence of (i) a halogen or halogen compound promoter and (ii) a noble metal-containing catalyst comprising a noble metal bonded to an inorganic oxide having surface hydroxyl groups through the intermediacy of a silicon containing component prepared by reacting a silicon containing compound of formula

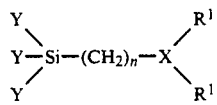

wherein
   (a) the Y groups are independently selected from the group consisting of ester, halide, or —OR groups where R is an alkyl group,
   (b) n is a number from 1 to 6,
   (c) X is nitrogen, and
   (d) the R$^1$ groups are independently selected from hydrogen or alkyl groups or together in conjunction with X form a 5- or 6-membered heterocyclic ring with the surface hydroxyl groups of the inorganic oxide.

2. A process according to claim 1 wherein the noble metal component is rhodium.

3. A process according to claim 2 wherein the inorganic oxide having surface hydroxyl groups is either silica or alumina.

4. A process according to claim 1, wherein —Y is an —OR group in which R is either methyl or ethyl.

5. A process according to claim 1 wherein the silicon compound of formula (I) is either:

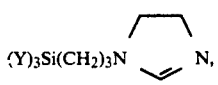
(A)

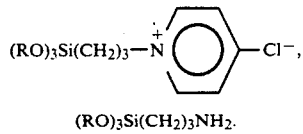
(B)

(RO)$_3$Si(CH$_2$)$_3$NH$_2$. (C)

6. A process according to claim 1 wherein the silicon compound is one having a nitrogen containing functional group capable of coordinating with the noble metal component which functional group is capable of quaternisation.

7. A process according to claim 1 wherein the alcohol used as a feedstock is an aliphatic alcohol having from 1 to 20 carbon atoms.

8. A process according to claim 7 wherein the alcohol is methanol and there is produced acetic acid and/or methyl acetate.

9. A vapor phase process for preparing a carboxylic acid having n+1 carbon atoms and/or an ester of said acid and an alcohol of n carbon atoms, which process comprises:
   (1) vaporising said alcohol,
   (2) contacting the vapor of said alcohol with carbon monoxide at a temperature of at least 50° C. in the presence of (i) a halogen or halogen compound promoter and (ii) a noble metal-containing catalyst comprising a noble metal bonded to an inorganic oxide having surface hydroxyl groups through the intermediacy of a silicon containing component prepared by reacting a silicon containing compound with the surface hydroxyl groups of the inorganic oxide wherein the silicon compound which is condensible with the hydroxyl groups has a functional group capable of reacting further with a nitrogen-containing functional group capable of coordinating with the noble metal component thereby to bond the nitrogen-containing functional group to the silicon compound and to bond the noble metal to the inorganic oxide through the intermediacy of a group having the formula:

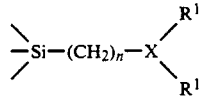

wherein n is a number from 1 to 6, X is nitrogen, and the R$^1$ groups are independently selected from hydrogen or alkyl groups or together in conjunction with X form a 5- or 6-membered heterocyclic ring.

10. A vapor phase process for preparing a carboxylic acid having n+1 carbon atoms and/or an ester of said acid and an alcohol of n carbon atoms, which process comprises:
   (1) vaporising said alcohol,
   (2) contacting the vapor of said alcohol with carbon monoxide at a temperature of at least 50° C. in the presence of (i) a halogen or halogen compound promoter and (ii) a noble metal-containing catalyst comprising a noble metal bonded to an inorganic oxide having surface hydroxyl groups through the intermediacy of a silicon containing component of formula:

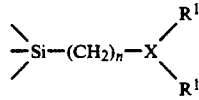

wherein n is a number from 1 to 6, X is nitrogen, and the R$^1$ groups are independently selected from hydrogen or alkyl groups or together in conjunction with X form a 5- or 6-membered heterocyclic ring.

* * * * *

UNITED STATES PATENT AND TRADEMARK OFFICE
CERTIFICATE OF CORRECTION

PATENT NO. : 5,185,462
DATED : February 9, 1993
INVENTOR(S) : JOHN EVANS and STEVEN L. SCRUTON It is certified that error appears in the above-identified patent and that said Letters Patent is hereby corrected as shown below:

Col. 7, line 57, should read "according to claim 1 or claim 2"

Col. 8, line 9, should read "having a nitrogen-containing"

Signed and Sealed this

Eighteenth Day of January, 1994

Attest:

BRUCE LEHMAN

*Attesting Officer*          *Commissioner of Patents and Trademarks*